US009393149B2

(12) United States Patent
Garth et al.

(10) Patent No.: US 9,393,149 B2
(45) Date of Patent: *Jul. 19, 2016

(54) DOUBLE PULL BODY BRACE

(71) Applicant: W.G. Holdings, LLC, Irvine, CA (US)

(72) Inventors: Geoffrey Garth, Long Beach, CA (US); Albert Romo, Lakewood, CA (US)

(73) Assignee: W.G. Holdings, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,460

(22) Filed: Feb. 16, 2015

(65) Prior Publication Data
US 2015/0157485 A1    Jun. 11, 2015

Related U.S. Application Data

(62) Division of application No. 13/490,739, filed on Jun. 7, 2012, now Pat. No. 8,956,315, which is a division of application No. 13/415,456, filed on Mar. 8, 2012, now Pat. No. 8,663,141, which is a division of application No. 10/977,726, filed on Mar. 2, 2005, now Pat. No. 8,142,377, which is a division of application No. 10/440,525, filed on May 19, 2003, now Pat. No. 7,003,148.

(51) Int. Cl.
A61F 5/00     (2006.01)
A61F 5/02     (2006.01)

(52) U.S. Cl.
CPC . A61F 5/02 (2013.01); A61F 5/028 (2013.01); A61F 2250/001 (2013.01)

(58) Field of Classification Search
CPC ..... A61F 5/028; A61F 2250/001; A61F 5/02; A61F 5/024; A61F 5/30; F03D 7/06; B23D 45/003; B23D 1/041; Y10T 29/49; Y10T 29/49947

USPC ............................... 602/19, 32; 128/874–875
See application file for complete search history.

(56) References Cited

U.S. PATENT DOCUMENTS

| 321,146 | A | | 6/1885 | Spencer |
| 2,554,337 | A | * | 5/1951 | Lampert ................ A61F 5/028 602/19 |
| 4,508,110 | A | | 4/1985 | Modglin |
| 5,179,942 | A | | 1/1993 | Drulias et al. |
| 5,188,586 | A | | 2/1993 | Castel et al. |
| 5,484,395 | A | | 1/1996 | DeRoche |
| 5,690,609 | A | | 11/1997 | Heinze, III |

(Continued)

OTHER PUBLICATIONS

Cybertech Body Jacket TLSO, Spine Brace, Cybertech Medical, Downloaded on Apr. 15, 2015.

*Primary Examiner* — Michael Brown
(74) *Attorney, Agent, or Firm* — Fish & Tsang LLP

(57) ABSTRACT

The double pull body brace comprises a one-piece panel which engages around the torso and overlaps at the front. At the overlap, it is attached to itself by means of a hook-and-loop fastener so that a wide range of adjustment is possible. In the back, spaced cord guides are mounted on said panel. Each cord guide carries a plurality of cord guide lobes. An upper cord is engaged around the upper cord guide lobes, and a lower cord is engaged around the lower cord guide lobes. These cords are separately attached to pull tabs. When donned, the user pulls on the pull tabs to separately adjust upper and lower closure tension of the body brace. When in correct adjustment, the pull tabs are attached in place by hook-and-loop fasteners.

20 Claims, 4 Drawing Sheets

(56) References Cited

U.S. PATENT DOCUMENTS

| | | |
|---|---|---|
| RE35,940 E | 10/1998 | Heinz et al. |
| 6,213,968 B1 * | 4/2001 | Heinz ................ A61F 5/028 602/19 |
| 6,322,529 B1 | 11/2001 | Chung |
| 6,676,620 B2 | 1/2004 | Schwenn et al. |
| 7,001,348 B2 * | 2/2006 | Garth ................ A61F 5/028 2/319 |
| 8,142,377 B2 * | 3/2012 | Garth ................ A61F 5/028 602/19 |
| 8,663,141 B2 * | 3/2014 | Garth ................ A61F 5/028 602/19 |
| 8,956,315 B2 * | 2/2015 | Garth ................ A61F 5/028 602/19 |
| 2001/0020144 A1 | 9/2001 | Heinz et al. |
| 2002/0148461 A1 | 10/2002 | Heinz et al. |
| 2005/0267390 A1 | 12/2005 | Garth et al. |
| 2012/0245502 A1 | 9/2012 | Garth et al. |

* cited by examiner

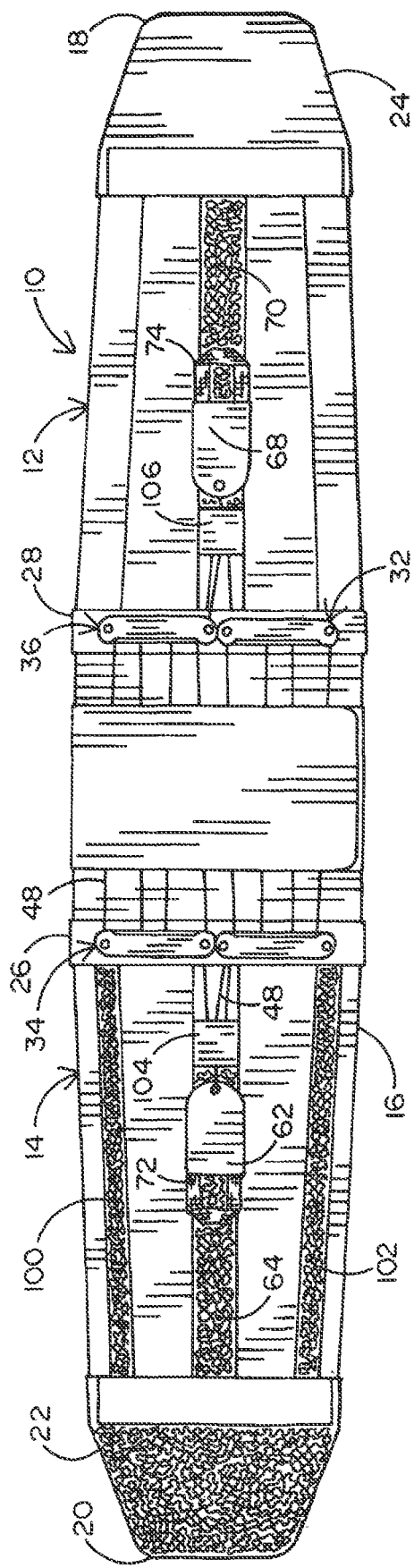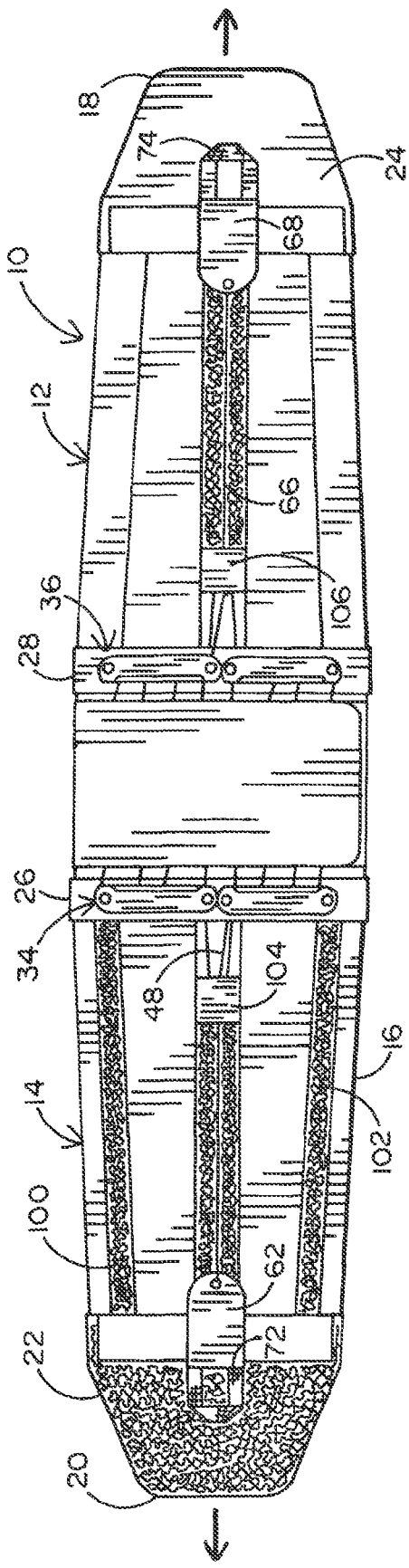

DOUBLE PULL BODY BRACE

This application is a divisional of patent application Ser. No. 13/490,739 filed Jun. 7, 2012, which is a divisional of patent application Ser. No. 13/415,456 filed Mar. 8, 2012 which issued as U.S. Pat. No. 8,663,141 on Mar. 4, 2012, which is a divisional of patent application Ser. No. 10/977,726, filed Oct. 28, 2004 which issued as U.S. Pat. No. 8,142,377 on Mar. 27, 2012, which is a divisional of patent application Ser. No. 10/440,525, filed May 19, 2003 which issued as U.S. Pat. No. 7,001,348 on Feb. 21, 2006. These and all other extrinsic materials discussed herein are incorporated by reference in their entirety.

FIELD OF THE INVENTION

This invention is directed to a lumbar support which is formed by a one-piece wraparound body panel with front closure and a back tightening system. The tightening system has right and left pull tabs which separately tighten the upper and lower potions of the body panel.

BACKGROUND OF THE INVENTION

Orthotic devices are provided for partial or substantial immobilization of the torso to stabilize the back. These orthotic devices are back braces which can be fitted snugly around the torso. Such back braces are effective in achieving spinal stability if worn properly. For many users, back braces are difficult to appropriately position and fasten. Without being consistently worn and properly adjusted, the effectiveness is substantially reduced. One problem with back braces is their need to conform to the torso as it changes. The torso may change from moment to moment as the patient moves between the standing and the sitting positions. In addition, the torso may change over the long term depending upon the nutritional and exercise habits of the wearer. To be fully effective, it is necessary that the back brace be tight. A system must be provided which can be easily and accurately adjustable by the wearer to provide both comfort and support in each posture so that proper spinal support is achieved.

Efforts have been made to provide convenience for the wearer in adjusting the body brace. Chung U.S. Pat. No. 6,322,529 teaches the use of force multiplication to increase closing force, but this is unbalanced. Heinz U.S. Pat. No. 6,213,968 teaches separately tightening the top and bottom of his body brace, but this is unbalanced. Furthermore, the Heinz patent teaches the use of a pulley system which is complicated in the number of parts which brings reliability problems in service.

SUMMARY OF THE INVENTION

In order to aid in the understanding of this invention, it can be stated in essentially summary form that it is directed to a body brace. The body brace has a single one-piece wraparound body panel with an overlapping front closure thereon. Attachments are made at the back of the panel so that two tightening cords sinuously engage upper and lower portions of the body panel. When these cords are pulled, the body panel is shortened. The cords are arranged so that one cord pulls to the right to pull the top closed, and the other cord pulls to the left to pull the bottom closed. This is arranged by attaching two upper cord guides on the single body panel spaced from each other and two lower cord guides on the single body panel spaced from each other. The top cord guides have lobes thereon around which the top tightening cord extends. The bottom cord guides have lobes thereon around which the bottom tightening cord extends. A cap covers the lobes to retain the cords in place. Pockets may be provided for the receipt of stiffeners or temperature packs.

It is, thus, a purpose and advantage of this invention to provide a one-piece body brace which wraps around the torso and is secured by overlapping fasteners to minimize twisting in the plane of the fasteners.

It is a further purpose and advantage of this invention to provide a one-piece body panel wraparound body brace formed of a one-piece body panel which engages around the torso of the patient. Upper and lower sinuous cords are engaged on separate top and bottom one-piece molded cord guides which are laterally spaced from each other and secured onto the one-piece body panel so that, when the cords are pulled in opposite directions, the panel is effectively shortened. Separate tightening of the upper and lower cords achieves separate tightening of the upper and lower portions of the body panel. Pulling in opposite directions provides balance to the pulling forces for beneficial ergonomic effect.

It is a further purpose and advantage of this invention to provide a body brace which is formed of a one-piece wraparound body panel which has spaced cord guides attached thereto. These cord guides are molded of synthetic polymer material which presents a plurality of cord guide lobes around which the tightening cord is engaged, providing a cord guide system which is simple, lightweight and free of unnecessary moving parts.

It is a further purpose and advantage of this invention to provide a one-piece wraparound body brace which is easy to don and which can easily be adjusted by the user as he changes position and has a pocket under the tightening cords which can contain a temperature or cushion pad so that the body brace remains comfortable and yet provides full support as the user moves from one posture to another, due to the mechanical advantage of the tightener, so that it can be conveniently and accurately adjusted by the user, as is needed for comfort and support.

It is another purpose and advantage of this invention to provide a body brace which can be quickly and easily fitted to the individual so that the user can readily take advantages of the comfort and support of a properly supplied back brace.

Other purposes and advantages of this invention will become apparent from a study of the following portion of the specification, the claims and the attached drawings.

BRIEF DESCRIPTION OF THE DRAWINGS

FIG. 2 is a similar view, shown with the pockets closed.

FIG. 3 is a similar view shown with the cords pulled so that the net overall length of the back brace is reduced.

DESCRIPTION OF THE PREFERRED EMBODIMENT

Figure 1:
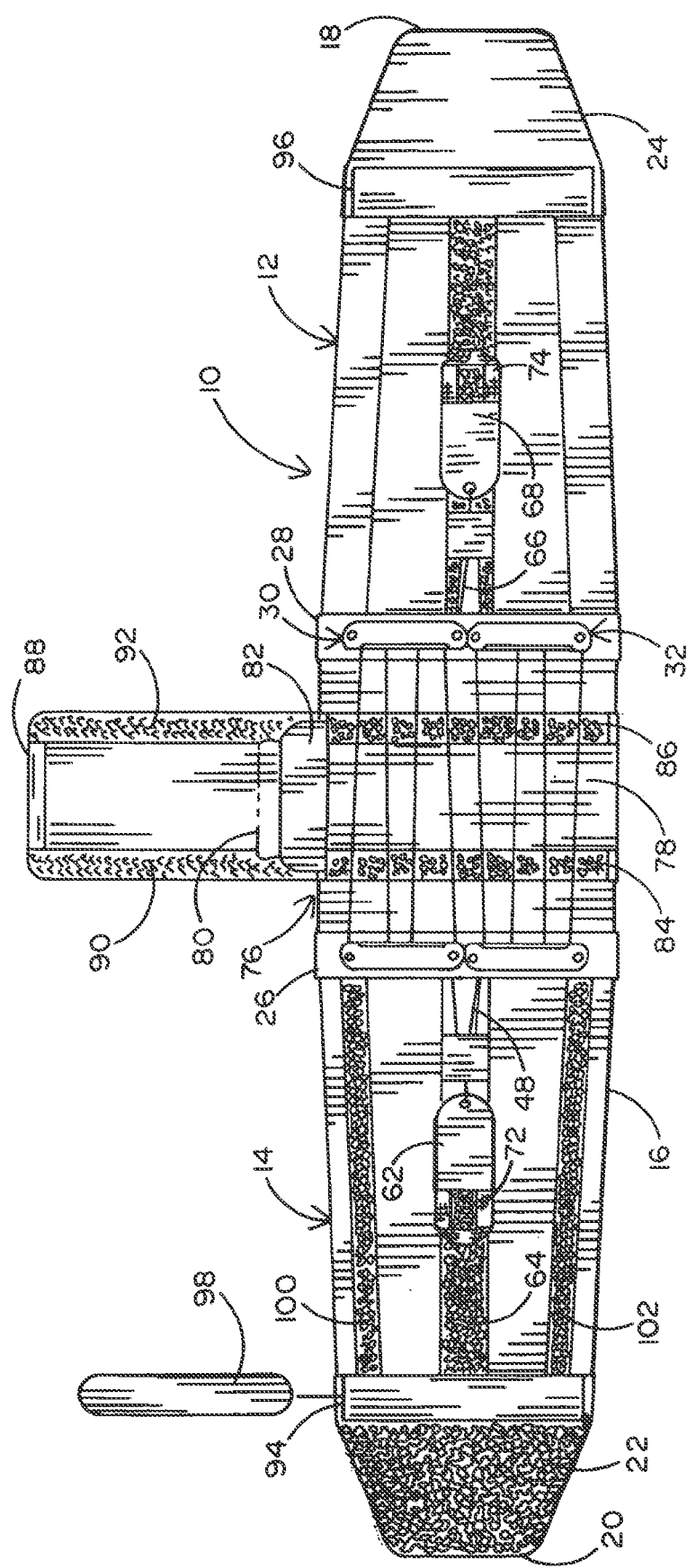
FIG. 1 is an outside view of the double pull body brace of this invention in the flat position with the pockets opened and the inserts therein shown in exploded position.

The preferred embodiment of the one-piece back brace of this invention is generally indicated at 10 in FIGS. 1, 2, 3 and 6. The back brace 10 has a one-piece panel which extends from top edge 14 to bottom edge 16 and from right end 18 to left end 20. This orientation is seen by the wearer as he dons the back brace. He holds the back brace behind him with the right end to his right and the top edge upward and engages it around his torso. The panel 12 is flexible and easily wraps around his torso with the ends overlapping. A hook-and-loop fastener system in the overlap area engages the left and right ends to hold them as desired. Loop assembly 22 is attached to the outside of the panel 12 adjacent its end to form the loop panel. A hook panel is secured to the underside of attachment panel 24 adjacent the right end. The material of the one-piece panel 12 may be synthetic polymer sheet material of good flexibility or may be a polymer netting material. The panel 12 is preferably made of flexible, breathable, substantially non-stretchable in the longitudinal direction synthetic polymer mesh fabric. The top and bottom edges of the panel are protected and strengthened by bias tape folded over and attached at the edges. The wearer places it upon himself with the panel 12 in the extended position and pulls the back brace tight around his torso at the position he desires. He can form it into slightly conical shape before the hook-and-loop system is engaged because the hook-and-loop system is amenable to attachment in different angular positions when the angle is considered in the plane of attachment.

The pulling tight of the panel around the torso with subsequent attachment of the hook-and-loop fastener system is not sufficient to provide adequate tension in the back brace. To provide for further controllable tightening, a tightening system is provided. Attachment straps 26 and 28 are secured to the outside of panel 12 toward the back and spaced from each other. An upper cord system 30 and a lower cord system 32 are mounted on the attachment straps. The upper cord system 30 is shown in more detail in FIGS. 4 and 5. Upper left cord guide 34 is attached to the upper half of attachment strap 26, and upper right cord guide 36 is attached to the upper half of attachment strap 28.

Figure 4:
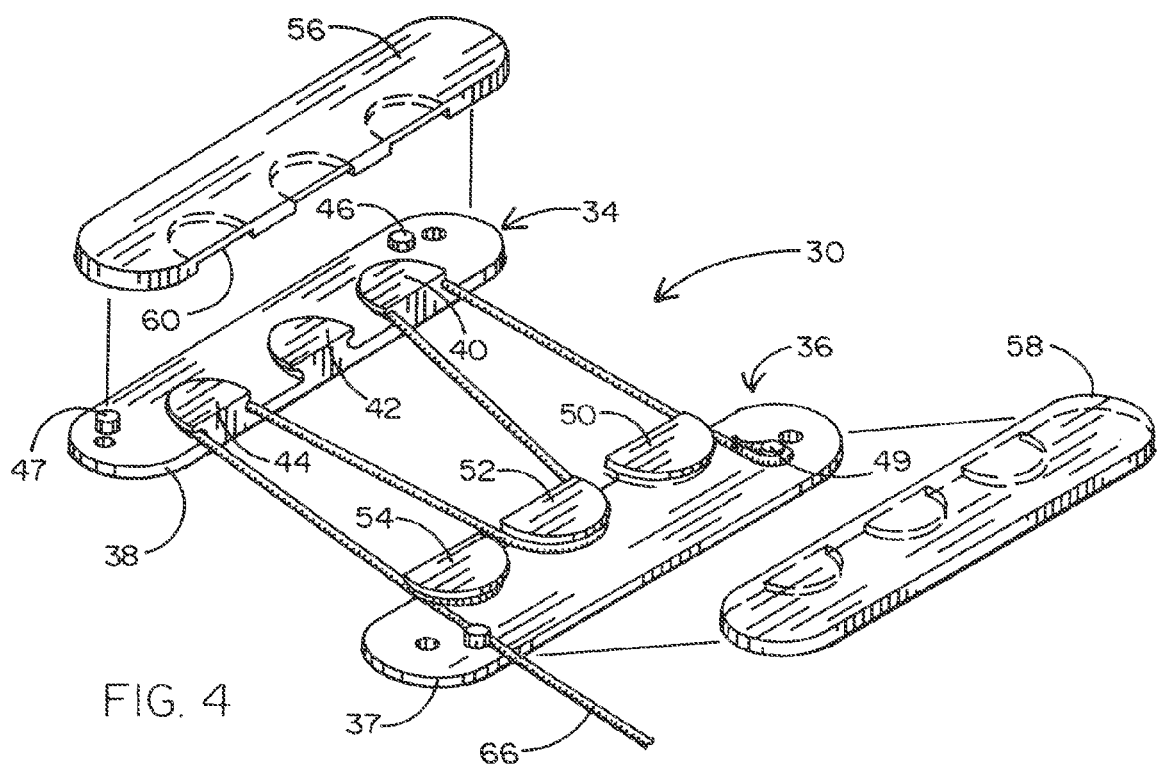
FIG. 4 is an enlarged exploded view of one of the sets of tightening cord guides and associated cord.
Figure 5:
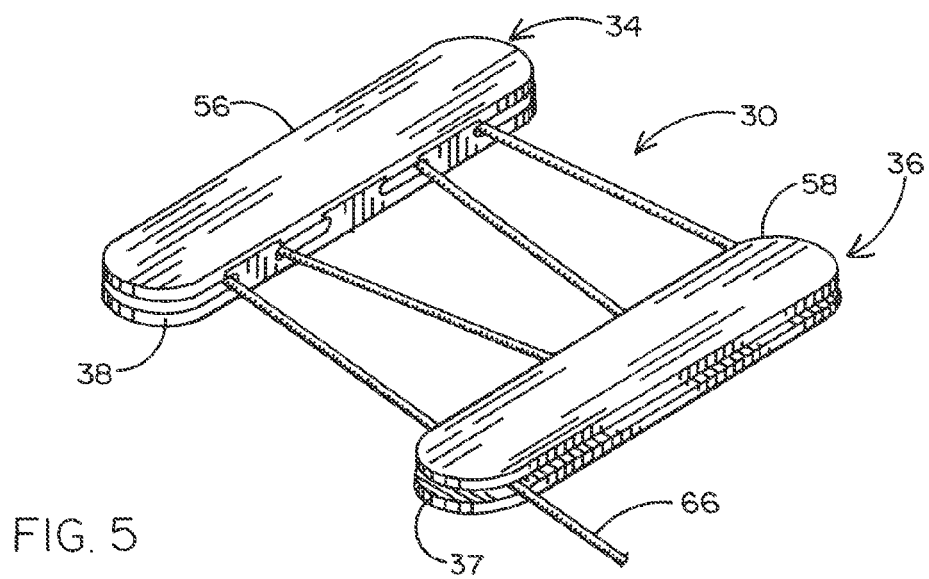
FIG. 5 is a similar view, showing the cord guide parts in the assembled position.

The construction of the upper left and upper right cord guides, is best seen in FIG. 4. The lower cord guides are constructed the same. The upper left cord guide has an upper left cord guide base 38 which has three cord guide lobes 40, 42 and 44 thereon. In addition, the base 38 has tie posts 46 and 47. The cord guide lobes are half round and are undercut on their half circumference. The under cut is circular in profile and is at least as large as the diameter of the cord. The under cuts are smooth so that cord 66 can be engaged therearound and smoothly moved around the lobes. For smooth movement, it is preferable that the cord guides 34 and 36 be made of a low friction polymer, such as nylon or Teflon. The upper right cord guide 36 is identical to upper left cord guide 34 and also has three cord guide lobes 50, 52 and 54 on its base 37. The cord guides are identical for manufacturing reasons, but they are not used in quite the same way. The cord 66 has an eye thereon engaged over post 49 on cord guide 36. The cord engages around lobe 40, lobe 52 and thence lobe 44 to extend out over the base 37. When the cord 66 is pulled to the right, as seen in FIG. 4, the cord guides 34 and 36 are pulled together with a 4-to-1 mechanical advantage (neglecting friction). The cord 66 is preferably a strong cord with low friction characteristics with respect to the cord guide lobes such as nylon.

In order to hold the cords in place on the lobes, caps 56 and 58 are provided to cover the bases of the cord guides. The caps have half round recesses, one of which is seen at 60, to engage over the lobes. The recess 60 engages on the top of lobe 44 to hold the cord in the undercut below the top of lobe 44, see FIG. 5. The caps also hold the cord loop on the post 49. The caps can be attached in any convenient way, such as snap on bosses, by adhesives or welding.

As seen in FIGS. 1, 2 and 3, the above-described upper cord system is attached on the upper part of the attachment straps 26 and 28, leaving a considerable space therebetween. An identical system of cord and cord guides, identified as lower cord system 32, is attached to the same straps 26 and 28, but below them. The upper cord system has its cord 66 extending to the right and attached to the right pull tab 68. The right pull tab 68 has the hook portion of a hook-and-loop attachment system on its underside. It is attachable to band 70 which is the loop portion of the hook-and-loop system. In FIGS. 1 and 2, the left pull tab 62 is attached close to the left attachment strap 26 because the distance between attachment straps is pulled out to its maximum. Similarly, cord 48 is a tightening cord of the lower cord system 32. It is attached to a left pull tab 62, which has the portion of a hook-and-loop system on its underside. It is fastenable in a selected location along band 64, which comprises the loop portion of the system. The band 64 is attached to the panel 12 along its longitudinal center line. The fact that the left and right pull tabs are pulled opposite each other in the back brace tightening process provides substantially balanced pull so as to eliminate the rotation of the back brace around the wearer's torso. In order to control the cords 48 and 66, panels 104 and 106 overlie them where they come away from the lower and upper cord systems on their way to the pull tabs. These panels have hooks underneath them to engage upon the loop fasteners. The cords move under these panels with a small amount of drag, which is provided by the hook-and-loop fasteners in order to prevent extraneous looping of the cords with possible tangling.

The back braces are donned with the right and left ends are stretched out as far away from each other as possible, as seen in FIG. 2. The panel is wrapped around the torso and is closed by attaching the hooks under attachment panel 24 onto the loops of loop assembly 22. In normal fit, the hooks under attachment panel 24 engage in the loop assembly 22. However, for wearers with small torsos, the overlap may be greater. For this reason, strips 64, 100 and 102 of loop material extend along the outside of the back panel inward from the left end loop assembly 22. When the overlap is greater, the hooks under the attachment panel 24 engage upon these loop strips 100 and 102. Once the basic positioning and fit are accomplished and the hook-and-loop attachment system of the left and right end is engaged, the wearer grasps the pull tabs 62 and 68, frees them from their hook-and-loop attachment, and pulls laterally with respect to his body with the right pull tab 68 pulled to the right and the left pull tab 62 pulled to the left.

Figure 6:
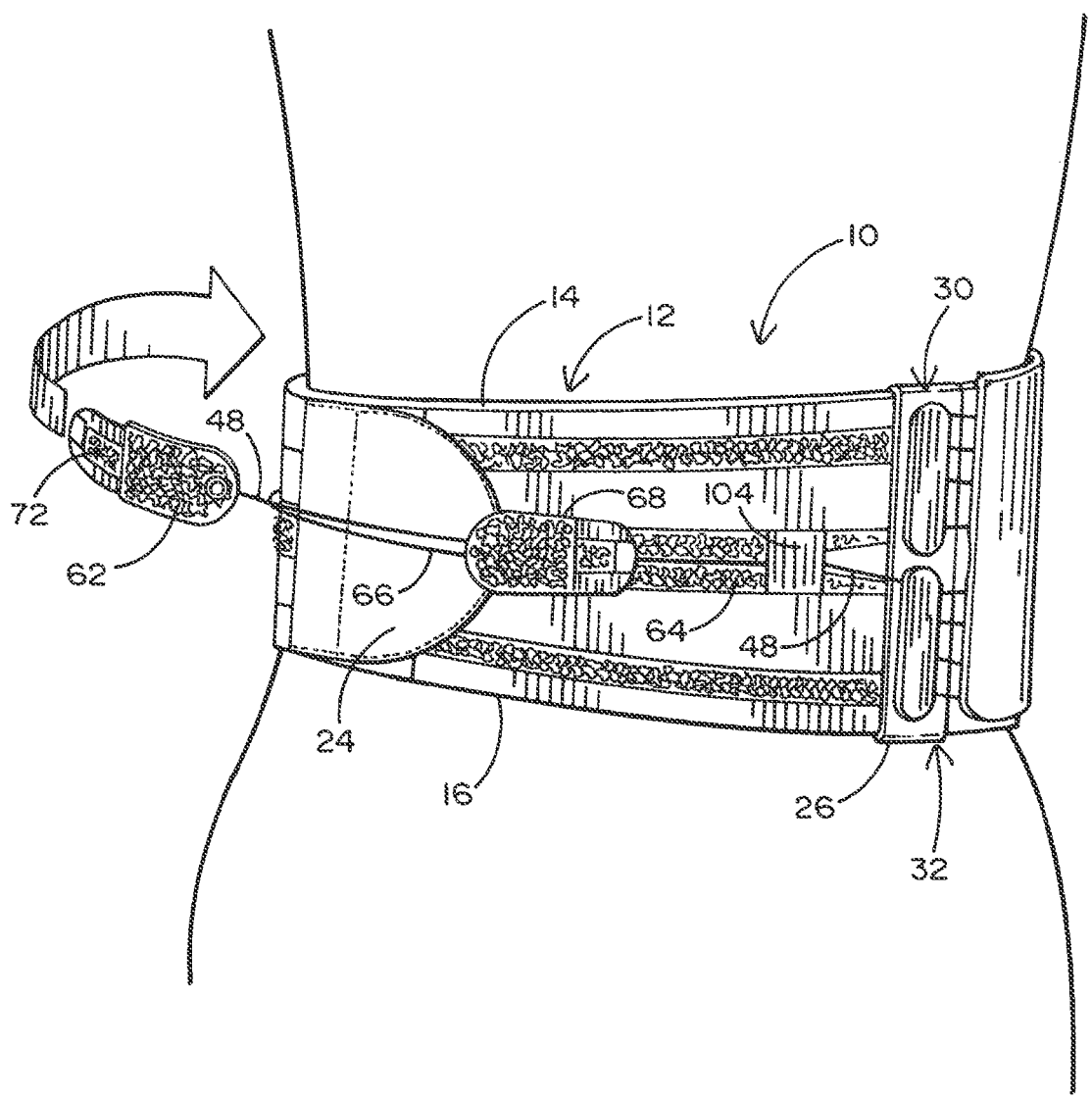
FIG. 6 is a left-side view of the double pull body brace on the torso of the wearer, showing the tightening of the back brace.

As seen in FIG. 6, the tabs are pulled around and across the overlapping front fastener and are attached on the opposite hook-and-loop fastener. This motion brings the tabs forward to where the wearer can use maximum force in pulling the body brace into the proper adjustment. Loop 72 has a loop of ribbon attached to the outer end of the pull tab so that the user may engage his thumb therethrough for a better grasp on the pull tab 62. Similarly, loop 74 has a ribbon loop attached to the outer end of the right pull tab 68 to make a stronger and more convenient grasp of the pull tab during tightening of the double pull body brace 10 on the torso of the wearer. Since the right pull tab 62 tightens the upper cord system and the left pull tab 68 tightens the lower cord system, the upper and lower sections can be adjusted to different tightness to provide for different body contours and to provide for support situations.

The one-piece panel 12 extends from one end to the other of the back brace and is sufficiently flexible so that, intermediate the attachment straps 26 and 28, the panel can wrinkle as the back brace is tightened. In addition, pocket 76 is formed on the panel 12 between the attachment straps 26 and 28. Pocket panel 78 is attached to the outside of the panel 12 on the visible side seen in FIG. 1. It forms a pocket into which a cushion pad of polymer foam or a hot or cold pack 80 can be inserted. In addition, foam pad 82 can also inserted into the pocket on the outside of the cold pack to conserve the chilling effect. The pocket 76 carries, on its left and right, strips 84 and 86 of the loop half of a hook-and-loop fastener. Pocket flap 88 carries the corresponding hook strips 90 and 92 of the hook-and-loop fastener combination. The strips 84 and 86 underlie the cords 48 and 66. When the pocket flap 88 is brought down from the open position in FIG. 1 to the closed position in FIGS. 2 and 3, the corresponding hook-and-loop strips interengage, and they interengage over the back and forth path of the cords. This serves to provide cord management. However, the position of the pocket limits the amount of closure one can achieve by pulling on the cords. It is limited to the space between the pocket 76 and the attachment straps 26 and 28. These are seen in the extended position in FIG. 2 and in the body brace tightening position in FIG. 3. As previously stated, the portion of the one-piece panel wrinkles up in those zones, but does not cause discomfort to the wearer.

In addition, pockets 94 and 96 are positioned against the left end of loop assembly 22 adjacent the right end attachment panel 24. These can receive stiffeners, such as stiffener 98 shown at the left end of FIG. 1 if the individual application requires such a device.

This invention has been described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A tightening system for a body brace, comprising:
   a first cord system having a first cord that sinuously engages a first set of cord guide lobes, wherein the first cord is disposed to cross a medial sagittal plane of a wearer at least two times when worn;
   a second cord system having a second cord that sinuously engages a second set of cord guide lobes, wherein the second cord is disposed to cross the medial sagittal plane of the wearer at least two times when worn; and
   wherein the first cord is positioned to engage the first set of cord guide lobes and the second cord is positioned to engage the second set of cord guide lobes such that, when worn by the wearer, the tightening system can be separately tensioned at the first cord system by pulling the first cord in a first direction, and at the second cord system by pulling the second cord n a second direction different from the first direction.

2. The tightening system of claim 1, wherein pulling on the first cord in the first direction effectively shortens a length of a first portion of the brace, and pulling on the second cord in the second direction effectively shortens a length of a second portion of the brace.

3. The tightening system of claim 1, further comprising a pull tab affixed to the first cord.

4. The tightening system of claim 3, further comprising a flexible panel extending from a back portion to a front portion of the torso of the wearer, wherein the pull tab removably attaches to the flexible panel using hook and loop fasteners.

5. The tightening system of claim 1, wherein the first set of cord guide lobes comprises at least two cord guide lobes, each of which are molded to form an integral piece.

6. The tightening system of claim 5, wherein the at least two cord guide lobes are non-rotating.

7. The tightening system of claim 1, wherein the first set of cord guide lobes comprises at least three cord guide lobes.

8. The tightening system of claim 1, wherein the first cord is disposed to cross the medial sagittal plane of the wearer at least three times when worn, and the second cord is disposed to cross the medial sagittal plane of the wearer at least three times when worn.

9. The tightening system of claim 1, wherein the first cord system is disposed vertically above the second cord system when worn by the wearer, and wherein the first cord is disposed such that pulling the first cord in the first direction effectively shortens a length of an upper portion of the brace, and the second cord is disposed such that pulling on the second cord in the second direction effectively shortens a length of a lower portion of the brace when worn by the wearer.

10. The tightening system of claim 1, wherein the first direction is a direction to the right of the medial sagittal plane, and the second direction is a direction to the left of the medial sagittal plane.

11. A body brace comprising the tightening system of claim 1.

12. The brace of claim 11, further comprising a flexible panel, wherein the flexible panel extends across the medial sagittal plane of the wearer when the brace is worn, and wherein pulling the first cord in the first direction causes the panel to wrinkle.

13. The brace of claim 11, further comprising a flexible panel extending from a back portion to a front portion of the torso of the wearer when worn.

14. The brace of claim 13, wherein the flexible panel is a one-piece panel.

15. A body brace for a lower back of a wearer, comprising:
   a first flexible panel portion extending from a back portion to a front portion of the wearer;
   a second flexible panel portion extending from the back portion to the front portion of the wearer;
   a third flexible panel portion disposed between the first and second flexible panel portions and extending across a lower back of the wearer;
   a first cord system having a first cord that sinuously engages a first set of cord guide lobes, and is disposed to cross a first sagittal plane of the wearer, and across the third panel portion;
   a second cord system having a second cord that sinuously engages a second set of cord guide lobes, and is disposed to cross a second sagittal plane of the wearer, and across the third panel portion; and
   wherein the first and second cords, the first set of cord guide lobes, and the second set of cord guide lobes are operatively coupled to the third panel portion such that the pulling on the first and second cords in opposite directions causes the third panel portion to wrinkle, and re-adjusts the brace about the torso of the wearer when the brace is worn.

16. The brace of claim 15, wherein the first and second cords, the first set of cord guide lobes, and the second set of cord guide lobes are operatively coupled to the third panel portion such that the body brace can be separately tensioned at the first cord system and the second cord system by pulling at least one of the first and second cords.

17. The brace of claim 15, further comprising a pull tab that is affixed to one of the first and second cords, and that removably attaches to at least one of the first, second and third panel portions using hook and loop fasteners.

18. The brace of claim 15, wherein the first set of cord guide lobes includes a first cord guide lobe disposed on a left side of the third panel portion, and a second cord guide lobe disposed on a right side of the third panel portion.

19. The brace of claim 15, wherein the second sagittal plane is the first sagittal plane.

20. The brace of claim 15, wherein the third panel portion comprises a separate material from the first panel portion, and is disposed under the first and second cords when the brace is worn.

* * * * *